United States Patent
Everett et al.

(10) Patent No.: US 7,433,046 B2
(45) Date of Patent: Oct. 7, 2008

(54) PATTERNED SPINNING DISK BASED OPTICAL PHASE SHIFTER FOR SPECTRAL DOMAIN OPTICAL COHERENCE TOMOGRAPHY

(75) Inventors: Matthew J. Everett, Livermore, CA (US); Scott A. Meyer, Livermore, CA (US); Yan Zhou, Pleasanton, CA (US)

(73) Assignee: Carl Ziess Meditec, Inc., Dublin, CA (US)

( * ) Notice: Subject to any disclaimer, the term of this patent is extended or adjusted under 35 U.S.C. 154(b) by 752 days.

(21) Appl. No.: 10/933,795

(22) Filed: Sep. 3, 2004

(65) Prior Publication Data

US 2006/0072424 A1    Apr. 6, 2006

(51) Int. Cl.
*G01B 9/02* (2006.01)
(52) U.S. Cl. .................................... 356/479
(58) Field of Classification Search ............ 379/99; 356/479, 350, 507, 450; 369/112.01, 44.11; 372/94, 99, 102
See application file for complete search history.

(56) References Cited

U.S. PATENT DOCUMENTS

| | | | | |
|---|---|---|---|---|
| 4,448,529 A | * | 5/1984 | Krause | 356/310 |
| 4,491,730 A | * | 1/1985 | Pedersen | 250/343 |
| 5,283,796 A | | 2/1994 | Fink | 372/32 |
| 5,321,501 A | | 6/1994 | Swanson et al. | 356/345 |
| 5,459,570 A | | 10/1995 | Swanson et al. | 356/345 |
| 5,491,524 A | | 2/1996 | Hellmuth et al. | 351/212 |
| 5,627,847 A | * | 5/1997 | Leger | 372/9 |
| 6,111,645 A | | 8/2000 | Tearney et al. | 356/354 |
| 6,268,907 B1 | | 7/2001 | Samuels et al. | 355/71 |
| 6,282,011 B1 | | 8/2001 | Tearney et al. | 359/287 |
| 6,377,349 B1 | | 4/2002 | Fercher | 356/450 |
| 2002/0154672 A1 | | 10/2002 | Friesem et al. | 372/92 |
| 2004/0236230 A1 | | 11/2004 | Crowley et al. | 600/476 |

(Continued)

FOREIGN PATENT DOCUMENTS

WO    WO 98/50986    11/1998

(Continued)

OTHER PUBLICATIONS

A. P. Kol' chenko, Control of the structure of transverse laser modes by phase-shifting masks, Jan. 31, 1980, Soviest journal of quantum electronics, vol. 10, No. 8, pp. 1013-1016.*

(Continued)

*Primary Examiner*—Tarifur R Chowdhury
*Assistant Examiner*—Michael Lapage
(74) *Attorney, Agent, or Firm*—Stallman & Pollock LLP

(57) ABSTRACT

A low cost patterned spinning disk is disclosed for achieving relatively rapid discrete optical phase shifts for an optical beam. The invention is particularly useful in a spectral domain optical coherence tomography system. The disk contains stepped patterns of different heights and/or refractive index distribution such that as it spins, an optical beam passing through or being reflected by the disk will experience different discrete optical phase delays. The disk can be operated as a phase shifter or it can be operated in synchronization with an intensity modulating chopper disk or a direct intensity modulation of the light source. The disk can also contain intensity modulating patterns such that both phase shifting and intensity modulation can be achieved at the same time. Various possible methods are also disclosed for the fabrication of the disk.

41 Claims, 18 Drawing Sheets

U.S. PATENT DOCUMENTS

2005/0058352 A1* 3/2005 Deliwala .................. 382/232

OTHER PUBLICATIONS

N.G. Chen et al., "Rotary mirror array for high-speed optical coherence tomography," *Optics Letters*, vol. 27, No. 8, Apr. 15, 2002, pp. 607-609.

J.F. de Boer et al., "Improved signal-to-noise ratio in spectral-domain compared with time-domain optical coherence tomography," *Optics Letters*, vol. 28, No. 21, Nov. 1, 2003, pp. 2067-2069.

A.F. Fercher et al., "Measurement of intraocular distances by backscattering spectral interferometry," *Optics Communications*, vol. 117, May 15, 1995, pp. 43-48.

J.G. Fujimoto, "Optical coherence tomography for ultrahigh resolution in vivo imaging," *Nature Biotechnology*, vol. 21, No. 11, Nov. 2003, pp. 1361-1367.

D. Huang et al., "Optical Coherence Tomography," *Science*, vol. 254, Nov. 2, 1991, pp. 1178-1181.

M. Lai, "Kilohertz scanning optical delay line employing a prism array," *Applied Optics*, vol. 40, No. 34, Dec. 1, 2001, pp. 6334-6336.

R.A. Leitgeb et al., "Phase-shifting algorithm to achieve high-speed long-depth-range probing by frequency-domain optical coherence tomography," *Optics Letters*, vol. 28, No. 22, Nov. 15, 2003, pp. 2201-2203.

R. Leitgeb et al., "Performance of fourier domain vs. time domain optical coherence tomography," *Optics Express*, vol. 11, No. 8, Apr. 21, 2003, pp. 889-894.

L.M. Smith et al., "Absolute displacement measurements using modulation of the spectrum of white light in Michelson interferometer," *Applied Optics*, vol. 28, No. 15, Aug. 15, 1989, pp. 3339-3342.

M. Wojtkowski et al., "Real-time in vivo imaging by high-speed spectral optical coherence tomography," *Optics Letters*, vol. 28, No. 19, Oct. 1, 2003, pp. 1745-1747.

M. Wojtkowski et al., "Full range complex spectral optical coherence tomography technique in eye imaging," *Optics Letters*, vol. 27, No. 16, Aug. 15, 2002, pp. 1415-1417.

S.H. Yun et al., "Pulsed-source and swept-source spectral-domain optical coherence tomography with reduced motion artifacts," *Optics Express*, vol. 12, No. 23, Nov. 15, 2004, pp. 5614-5624.

Andrei B. Vakhtin et al., "Differential spectral interferometry: an imaging technique for biomedical applications," *Optics Letters*, vol. 28, No. 15, Aug. 1, 2003, pp. 1332-1334.

M.M. Varma et al., "Spinning-disk self-referencing interferometry of antigen-antibody recognition," *Optics Letters*, vol. 29, No. 9, May 1, 2004, pp. 950-952.

* cited by examiner

Thickness or refractive index Profile

Thickness or refractive index Profile

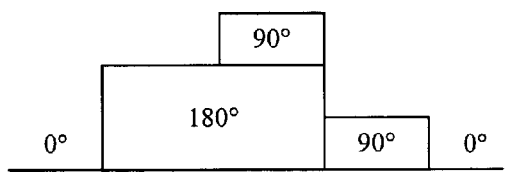 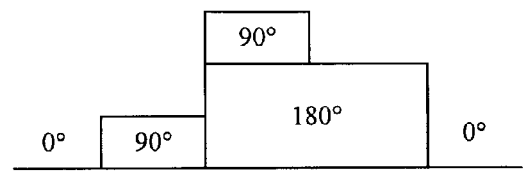
Fig. 3AFig. 3B

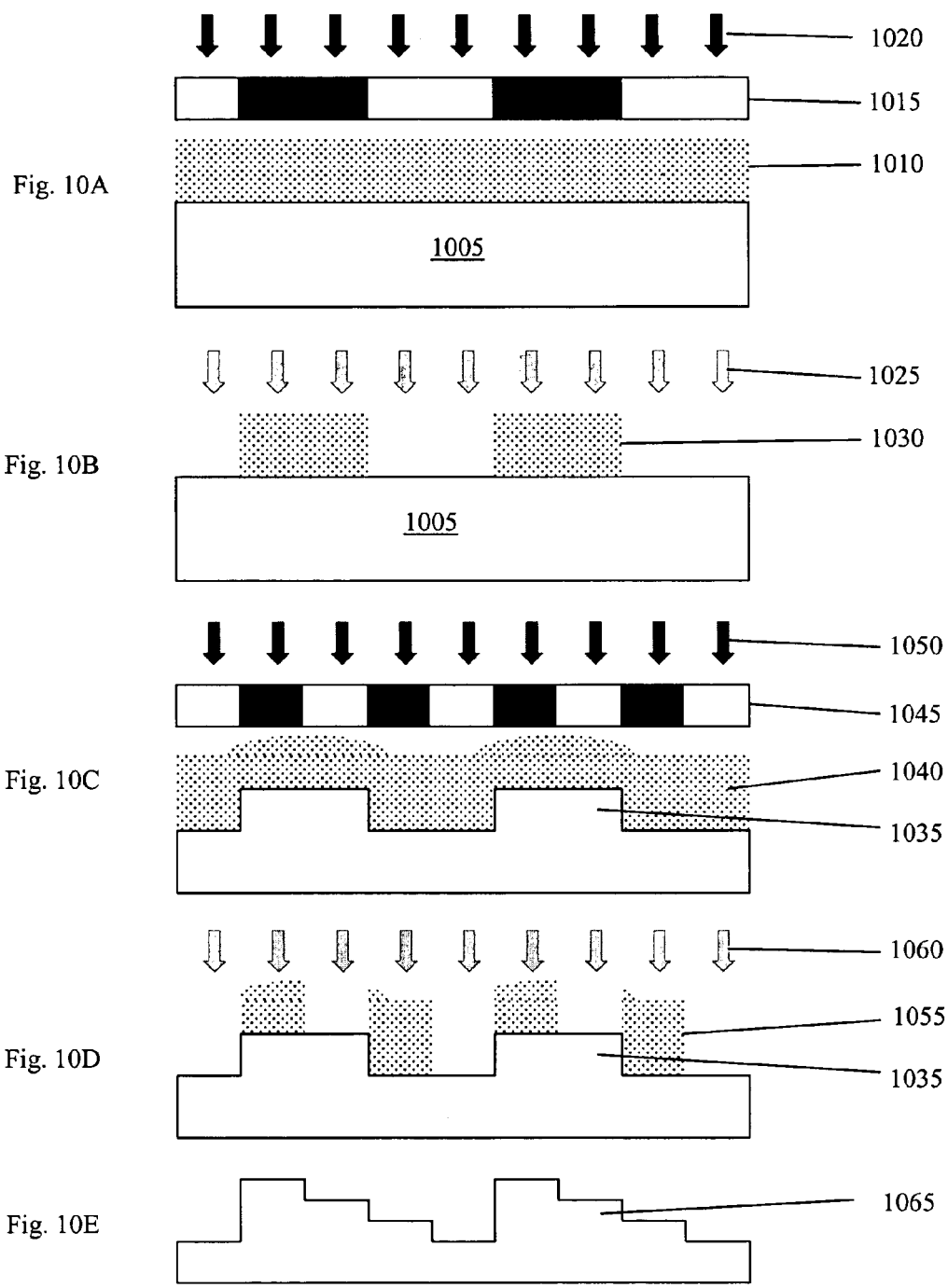

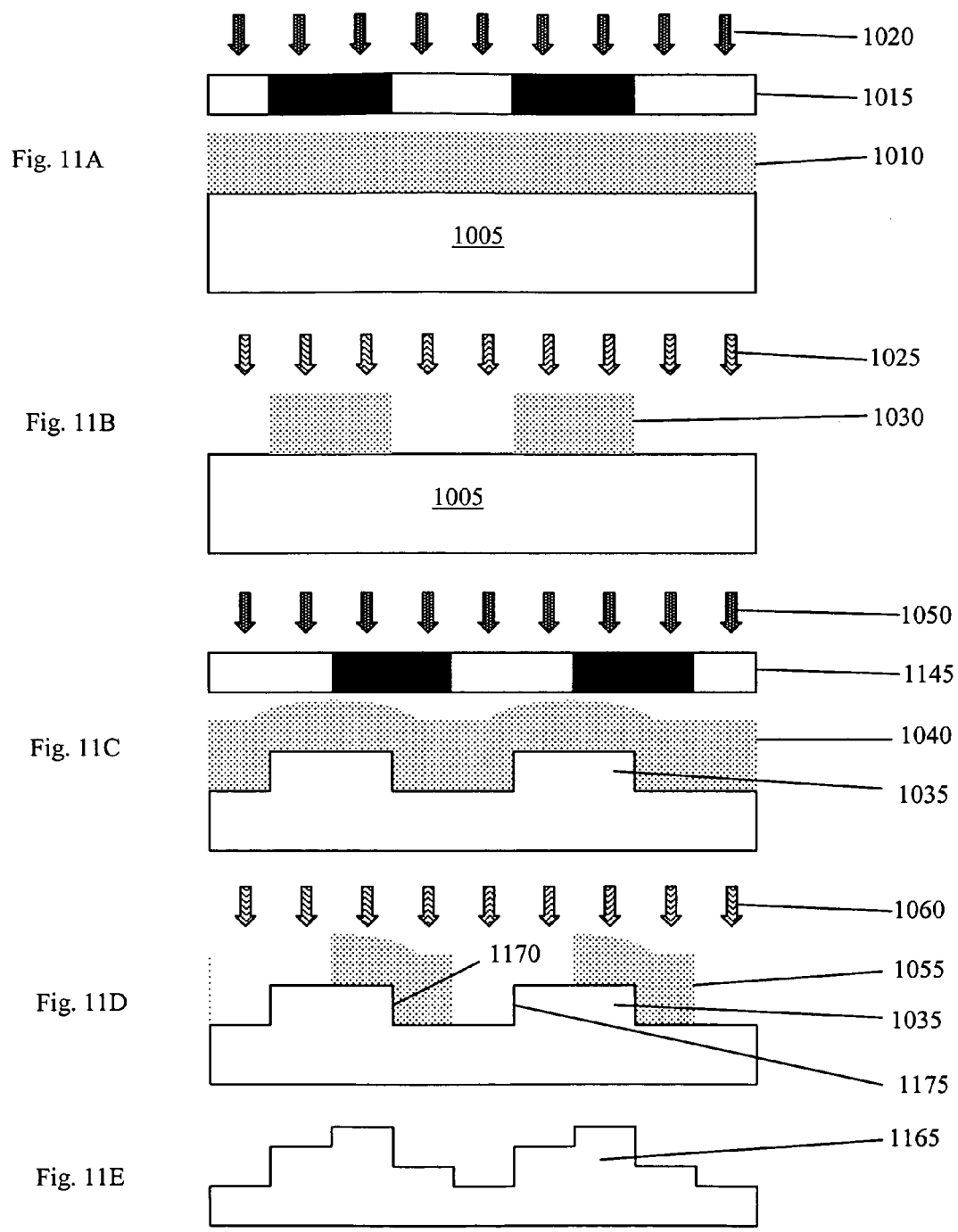

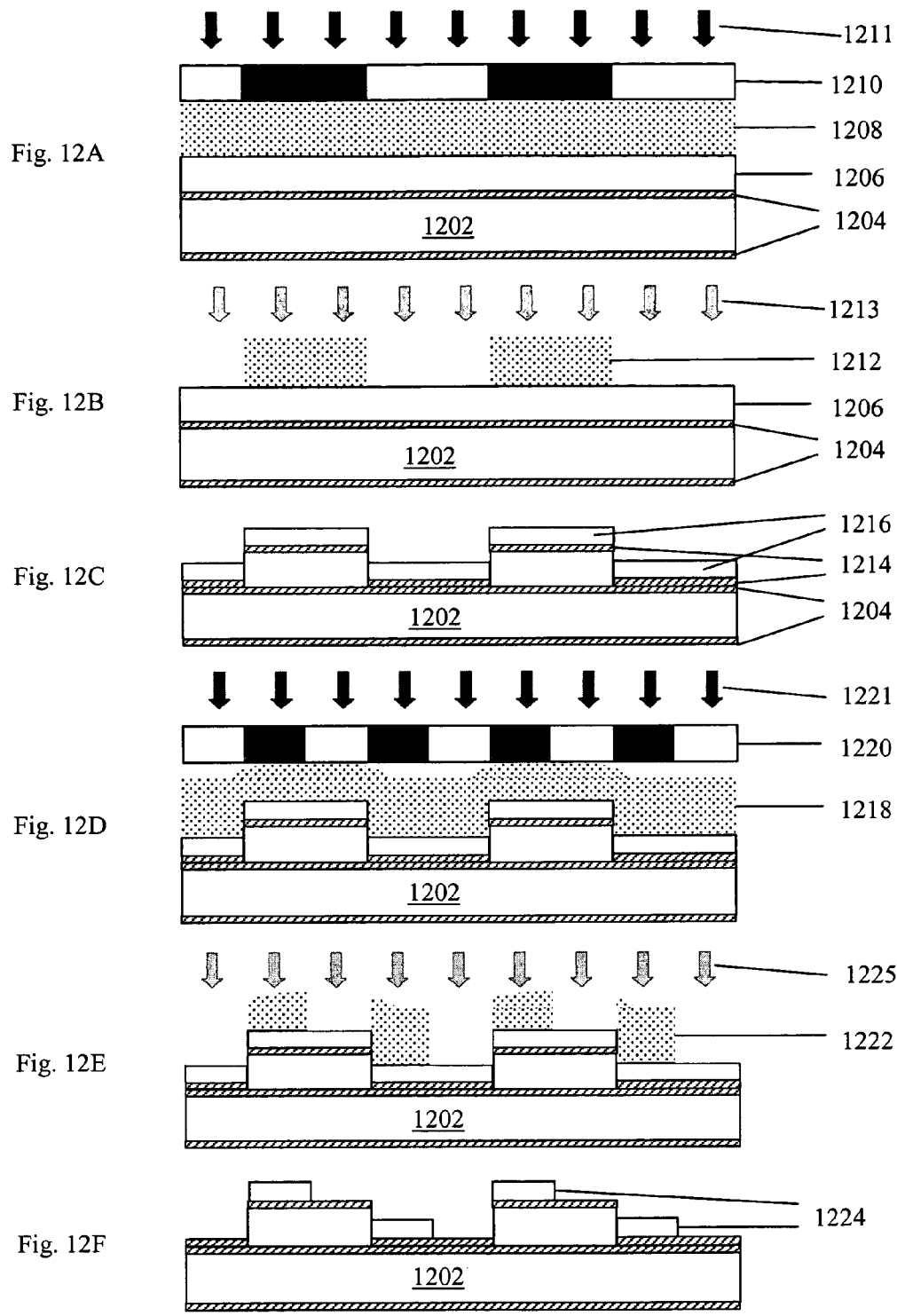

PATTERNED SPINNING DISK BASED OPTICAL PHASE SHIFTER FOR SPECTRAL DOMAIN OPTICAL COHERENCE TOMOGRAPHY

BACKGROUND OF THE INVENTION

1. Field of the Invention

The invention relates generally to optical phase shifting and in particular to apparatus and methods for achieving low cost and yet relatively rapid discrete phase shifting in optical interferometers.

2. Description of Related Art

Optical coherence tomography (OCT) is a technology that is based on low coherence optical interferometry to scan a sample in both the depth and transverse directions to generate a two or three dimensional image of the sample (Huang, D. et al. (1991). "Optical coherence tomography." *Science* 254 (5035): 1178-81; and Fujimoto, J. G. "Optical coherence tomography for ultrahigh resolution in vivo imaging." *Nat Biotechnol* 21(11): 1361-7, (2003)). This technology was first implemented in the time domain, in which the relative optical path length difference of the two interferometer arms is scanned, typically by moving a reference mirror mechanically as a function of time (U.S. Pat. Nos. 5,459,570, 5,321, 501). This approach limits image acquisition speed.

It was later demonstrated that spectral domain OCT has significant advantages in speed. In spectral domain OCT, the optical path length difference between the sample and reference arm is not mechanically scanned but rather, the interferometrically combined beam is sent to a spectrometer in which different wavelength components are dispersed onto different photodetectors to form a spatially oscillating interference fringe (Smith, L. M. and C. C. Dobson (1989). "Absolute displacement measurements using modulation of the spectrum of white light in a Michelson interferometer." *Applied Optics* 28(15): 3339-3342). A Fourier transform of the spatially oscillating intensity distribution can provide information on the reflectance distribution as a function of depth within the sample. As there is no mechanical depth scanning, acquisition of reflected light which covers a full depth range within the sample can be achieved simultaneously, and consequently, the speed of obtaining a full depth reflection image is substantially increased as compared to time domain OCT (Wojtkowski, M., et al. (2003). "Real-time in vivo imaging by high-speed spectral optical coherence tomography." *Optics Letters* 28(19): 1745-1747; Leitgeb, R. A., et al. (2003). "Phase-shifting algorithm to achieve high-speed long-depth-range probing by frequency-domain optical coherence tomography." *Optics Letters* 28(22): 2201-2203). In addition, as the light reflected from the full depth range within the sample is fully dispersed over many photodetectors, the shot noise for each photodetector is substantially reduced as compared to the time domain OCT case, and hence the signal to noise ratio can also be substantially increased (Leitgeb, R. A., et al. (2003). "Performance of Fourier domain vs. time domain optical coherence tomography." *Optics Express* 11(8): 889-894; De-Boer, J. F., et al. (2003). "Improved signal-to-noise ratio in spectral-domain compared with time-domain optical coherence tomography." *Optics Letters* 28(21): 2067-2069).

However, a direct Fourier transform of the interferogram is not sufficient to provide the information on the complex reflectance distribution within the sample. Such a direct Fourier transform contains both the autocorrelation and the cross-correlation interference terms and it does not reveal the phase between the sample and the reference reflector. Note that the superimposed intensity interferogram from a positive optical path length difference will be the same as that from a negative optical path length. To solve this problem, Fercher et al. used Fourier transformation of the complex spectral distribution, that is, a Fourier transformation of both the amplitude and the phase of the light beam (Fercher, A. F. et al. (1995). "Measurement of intraocular distances by backscattering spectral interferometry." *Optics Communications* 117(1-2): 43-48; and U.S. Pat. No. 6,377,349). In this method, the reference beam is changed in phase by discrete steps to separate the superimposed interferograms of difference phases, and the amplitude and phase of the sample beam are then obtained from the complex spectral distribution of the interferogram. An associated benefit of such a discrete relative phase shifting technique is that the usable depth coverage range is also doubled (Wojtkowski, M., A. Kowalczyk, et al. (2002). "Full range complex spectral optical coherence tomography technique in eye imaging." *Optics Letters* 27(16): 1415-1417; Leitgeb, R. A., et al. (2003) "Phase-shifting algorithm to achieve high-speed long-depth-range probing by frequency-domain optical coherence tomography." *Optics Letters* 28(22): 2201-2203). In addition, the DC background and the contribution from autocorrelation interference terms can also be removed (Vakhtin, A. B., et al. (2003). "Differential spectral interferometry: an imaging technique for biomedical applications." *Optics Letters* 28(15): 1332-1334).

However, all the prior art phase shifted SD-OCT system used a mirror attached to a piezoelectric ceramic stack or a mirror surfaced ceramic stack to achieve the desired discrete relative phase shift. This approach is slow due to the limited frequency response as well as the resonance of the ceramic stack. While there are already various types of optical phase shifters, modulators and optical path length delay lines as will be discussed shortly, the present invention discloses a novel way to achieve relatively high speed discrete optical phase shifting.

Optical phase shifting or modulation has been widely used in optical interferometry for various purposes, including optical wave front shaping, optical intensity modulation, and interferometric quadrature condition maintaining. In connection with interferometric optical fiber sensors, piezoelectric ceramic materials have been used to stretch a piece of fiber to achieve optical phase modulation. In free space based optical interferometers or laser cavities, mirrored piezoelectric ceramics have been used in reflection to achieve optical phase or path length modulation. Other electro or magneto-mechanically expandable or contractible materials such as piezoelectric polymers and magnetostrictive ceramics have also been used for similar purposes. However, these materials generally can only be operated up to a frequency of about several tens of kHz and they also have inherent resonance frequencies and hysteresis, and hence they cannot easily be operated to provide high speed stepped optical phase shifting. There are reports on fiber optic phase modulators that are made by coating thick lead zirconate titanate coaxially on the fiber which can achieve operating speeds within a range from hundreds of kilohertz to several megahertz. However, such a device is not commercially available yet and its cost is expected to be much higher than the present invention.

In optical fiber communications, electro-optic crystals and integrated optical waveguides are widely used for optical phase modulation. These optical phase modulators are based on the change in the refractive index of a crystal material in response to a change in the electrical or magnetic field or injected free-carriers applied to the material. They can be used to provide light intensity modulation using a Mach-Zehnder interferometer and the modulation speed is very high (up to tens of GHz). However, the cost of these devices is also high. In addition to the high cost, when a bulk crystal is used for optical phase modulation, the required voltage is also very high, whereas with integrated optical waveguide, light coupling into and out of the waveguide will most likely cause substantial light insertion loss as well as high cost associated with the packaging of the device.

Rotating devices have been used to vary the path length in time domain OCT systems. Examples include: a corner cube attached at an offset from a rotating shaft (U.S. Pat. Nos. 5,459,570, 5,321,501), a rotating helical mirror (U.S. Pat. No. 5,491,524), a rotating galvo mirror of a rapid scanning optical delay (RSOD) line (U.S. Pat. Nos. 6,111,645, 6,282,011), a rotary prism array (Lai, M. (2001). "Kilohertz Scanning Optical Delay Line Employing a Prism Array." *Applied Optics* 40(34): 6334-6336.) and a rotary mirror array (Chen, N. G. and Q. Zhu (2002). "Rotary mirror array for high-speed optical coherence tomography." *Optics Letters* 27(8): 607-609.). The purpose of these devices was to smoothly vary the path length of the reference arm relative to the sample arm of the time domain OCT system to vary the depth at which sampling occurs. The purpose of presently invented spinning disk is to shift the phase of the reference arm light relative to the sample arm in typically sub-wavelength increments over a range of approximately a wavelength to obtain quadrature information on the interference between the reference arm and the sample arm.

SUMMARY OF THE INVENTION

A patterned spinning disk based optical phase shifter, the method of fabricating the same, and its application to spectral domain OCT are disclosed. The patterned spinning disk contains discrete steps in terms of optical phase delay as a function of angle theta around the disk so that as the disk spins, the optical phase of a light beam propagating through or reflected from the disk is abruptly modified in a repetitive manner. The present invention is particularly useful for spectral domain optical coherence tomography.

In one aspect of the invention, the spinning disk is placed in one of the optical path of a spectral domain (also known as Fourier domain) optical coherence tomography (SD-OCT) system to rapidly change the relative phase (SD-OCT Phase Shifting Disk) of the interferometer or amplitude of the light beam (SD-OCT Chopper Disk).

Another aspect of the present invention is to provide a method for performing spectral domain optical coherence domain tomography comprising the steps of: guiding a low coherence light source through a broadband beam splitter into a sample arm leading to a sample, and a reference arm leading to a reflector; rapidly and repetitively shifting the relative optical phase between the sample arm and the reference arm and/or light intensity using the subject invented phase shifter; combining returned light waves from said sample and said reference reflector in said broadband beam splitter/combiner, guiding the combined light waves to a spectrometer for interference signal extraction and processing.

Another feature of the present invention is that the phase shifting function can be combined with intensity modulation on the same disk, with both phase shifting and intensity modulation synchronized.

Various methods of fabricating the phase shift disk are disclosed, which include various combinations of gray scale mask based photolithography, standard photolithography, wet or dry etching, multiple etch-stop and phase shift film deposition, lift-off, shadow mask based patterned film deposition, and embossing/stamping/molding.

One object of the invention is to obtain the full complex information of the spectral interferogram and to eliminate the DC term and the autocorrelation induced interference signals for background subtraction.

A second object is to double the usable depth coverage range by differentiating the positive and negative optical path length difference between the sample and the reference arms.

A further object of the invention is to substantially reduce the cost of rapid and repetitive optical phase modulation.

Another object is to reduce the duty cycle of the light beam by pulsing the light thereby allowing increased transverse scanning speed of the spectral domain OCT system.

Still another object of the present invention is to make it possible to synchronize the optical phase shifting with the pulsing of the light source and the data capturing of the spectrometer detector array.

These and other features and advantages of the present invention will become more readily apparent to those skilled in the art upon review of the following detailed description of the preferred embodiments taken in conjunction with the accompanying drawings.

BRIEF DESCRIPTION OF THE DRAWINGS

FIGS. 3A and 3B show two examples of non-equal phase delay step height 4-discrete-phase-shift arrangement.

FIGS. 10A to 10E show another exemplary method to fabricate the phase shift disk in which binary optics based multiple exposures and etchings are employed.

FIGS. 11A to 11E show another exemplary method to fabricate the phase shift disk with which minor mask misalignments will not introduce areas of unwanted phase shifts.

FIGS. 12A to 12F show the most preferred disk fabrication method in which layers for both etch-stop and phase change are deposited and patterned on a substrate.

DETAILED DESCRIPTION OF THE INVENTION

A patterned spinning disk based optical phase shifter is disclosed for achieving low cost and yet relatively rapid stepped discrete phase shifting in a spectral domain optical coherence tomography system. Such a disk can be operated as a single phase shifter or it can be operated in synchronization with an intensity modulating chopper disk or a direct intensity modulation of the light source. In addition, the phase shift disk can also be integrated with intensity modulating patterns on the same disk such that both phase shifting and intensity modulation can be achieved at the same time, which inherently ensures a synchronized modulation of both the phase and the intensity of either a single light path or more light paths, of a SD-OCT interferometer.

A very important feature of the present invention is the substantially lower cost of the phase shifter when compared to electro-optic crystal based optical phase shifters. When such a phase shifter is used in an SD-OCT system, it brings a number of advantages, including high-speed acquisition of the full complex spectral information of a spectral interferometer, high-speed background subtraction, the doubling of imaging depth coverage range, the intensity modulation of the laser beam shining onto the sample and hence reduction of the light pulse duty cycle, the synchronization of phase shift with intensity modulation and data acquisition, as well as others as will be made clear below.

Figure 1:
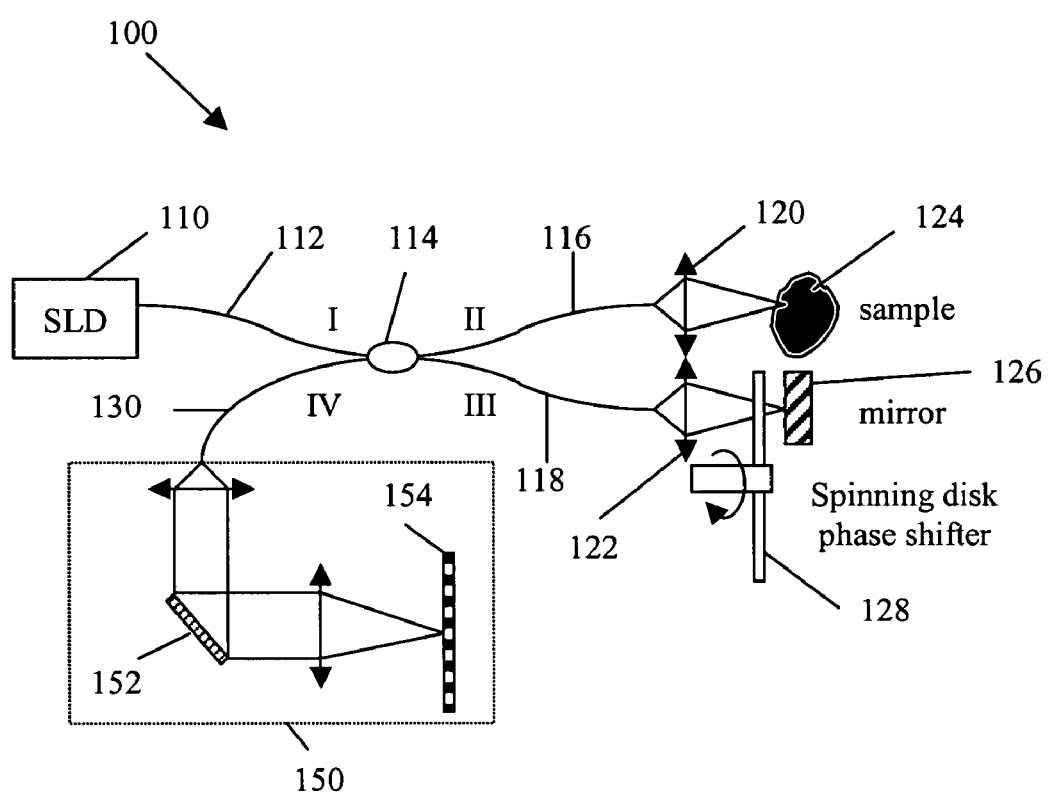
FIG. 1 shows a diagram of a spectral domain optical coherence tomography system according to a preferred embodiment of the present invention, in which a spinning disk based optical phase shifter is used.

FIG. 1 shows a diagram of a spectral domain optical coherence tomography system 100 according to one preferred embodiment of the present invention, in which a spinning disk based optical phase shifter is incorporated.

The light source 110 introduces broadband light to the system 100. The broadband light which can be any light source with a center wavelength within the optical spectrum range from ultra-violet to near infrared. It is preferably derived from a superluminescent diode (SLD), a light emitting diode (LED), a short pulsed laser such as a Ti:sapphire laser, a photonic crystal fiber laser or a spontaneous emission based rare earth doped optical fiber broad band light source. The light should have a bandwidth of at least 15 nm. As the bandwidth is increased, more information can be obtained. Solid state sources that have bandwidths up 150 nm are being developed and would be useful in this application. The light wave from the source 110 is preferably coupled through a short length of an optical fiber 112 to an input port (port I) of a fiber optic coupler 114, which splits the incoming light beam into the two arms of a Michelson interferometer. The two arms each has a section of optical fiber (116 and 118) that guides the split light beam from the two output ports (port II and port III) of the fiber coupler 114 to the sample 124 and the reference reflector 126 respectively. For both the sample arm and the reference arm, at the terminating portion of each fiber, there may be a module containing optical elements to collimate or focus or scan the beam. Illustrated in FIG. 1 as an embodiment are two focusing lenses 120 and 122. A patterned spinning disk based optical phase shifter 128 is placed in the reference arm for rapid phase (and intensity) modulation. The returned light waves from the sample 124 and the reference reflector 126 are directed back through the same optical path of the sample and reference arms and are combined in fiber coupler 114. A portion of the combined light beam is directed through a section of optical fiber 130 from port IV of the fiber coupler 114 to a spectrometer 150. Inside the spectrometer, the light beam is dispersed by a grating 152 and focused onto a detector array 154.

In terms of retrieving both the amplitude and the phase of the sample arm reflectance distribution based on the subject phase shifter, an exemplary embodiment is to obtain the interference signal at 4 discrete phases of $\pi/2$ phase difference. It is well known to those skilled in the art that the interfered light intensity is given by $$I(z,\lambda)=I_0+I'(z,\lambda)\cos[\phi(z,\lambda)+\phi(t)] \quad (1)$$

where z is the depth position of the reflected or scattered light from the sample, $\lambda$ is the wavelength of spectral component of the light source, $I_0$ is the DC component of the interfered light signal, $I'(z,\lambda)$ is the AC amplitude of the interference light signal to be found, $\phi(z,\lambda)$ is phase of the reflected light wave from the sample to be found, and $\phi(t)$ is the additional phase shift introduced by the spinning disk of the present invention. By rapidly shifting the additional relative phase from 0 to $\pi/2$ to $\pi$ to $3\pi/2$, we can obtain 4 interference signals as $$I_1(z,\lambda)=I_0+I'(z,\lambda)\cos[\phi(z,\lambda)], \phi(t_1)=0 \quad (2)$$

$$I_2(z,\lambda)=I_0-I'(z,\lambda)\sin[\phi(z,\lambda)], \phi(t_2)=\pi/2 \quad (3)$$

$$I_3(z,\lambda)=I_0-I'(z,\lambda)\cos[\phi(z,\lambda)], \phi(t_3)=\pi \quad (4)$$

$$I_4(z,\lambda)=I_0+I'(z,\lambda)\sin[\phi(z,\lambda)], \phi(t_4)=3\pi/2 \quad (5)$$

These can be combined to give us the complex spectral distribution of the reflected or scattered electric field from the sample as below:

$$A_1(z,\lambda) = I_1(z,\lambda) - I_3(z,\lambda) = I'(z,\lambda)2\cos[\varphi(z,\lambda)] \quad (6)$$
$$= I'(z,\lambda)\{\exp[i\varphi(z,\lambda)] + \exp[-i\varphi(z,\lambda)]\}$$

$$iA_2(z,\lambda) = i[I_4(z,\lambda) - I_2(z,\lambda)] = iI'(z,\lambda)2\sin[\varphi(z,\lambda)] \quad (7)$$
$$= I'(z,\lambda)\{\exp[i\varphi(z,\lambda)] - \exp[-i\varphi(z,\lambda)]\}$$

$$\frac{1}{2}\{A_1(z,\lambda) + iA_1(z,\lambda)\} = \frac{1}{2}\{[I_1(z,\lambda) - I_3(z,\lambda)] + i[I_4(z,\lambda) - I_2(z,\lambda)]\} \quad (8)$$
$$= I'(z,\lambda)\exp[i\varphi(z,\lambda)]$$

Note the spectrometer functions as a Fourier transformer because it gives the spectral distribution of the interferogram as a function of wavelength $\lambda$ or equivalently a function of the wavenumber $k=1/\lambda$. Hence by obtaining the spectral interferogram at the 4 different phases, one can easily obtain the complex Fourier transform of the field distribution. A reverse Fourier transformation of the complex spectral field distribution reveals the reflected or scattered electric field distribution as a function of the depth position z in the sample.

$$E(z)=FT^{-1}\{I'(z,\lambda)\exp[i\phi(z,\lambda)]\}= \quad (9)$$

With transverse scanning, a 3D tomogram of the sample can be obtained. It should be noted that the above-mentioned embodiment is only one of a number of schemes to retrieve the reflected or scattered electric field distribution in the sample. Instead of using 4 phase shifts, 2, 3 and 5 phase shifts have also been used and details of these schemes have been cited as references (Fercher, A. F. et al. (1995). "Measurement of intraocular distances by backscattering spectral interferometry." *Optics Communications* 117(1-2): 43-48; and U.S. Pat. No. 6,377,349; Wojtkowski, M., A. Kowalczyk, et al. (2002) "Full range complex spectral optical coherence tomography technique in eye imaging." *Optics Letters* 27(16): 1415-1417; Leitgeb, R. A., et al. (2003) "Phase-shifting algorithm to achieve high-speed long-depth-range probing by frequency-domain optical coherence tomography." *Optics Letters* 28(22): 2201-2203).

It should be understood that although the illustrated embodiment of FIG. 1 shows a fiber optics version, a free space optics version is a natural alternative. Further, the optical configuration can have some portions implemented using fiber optics and other portions implemented using free space bulk optics. The optical fiber used can be either standard single mode optical fibers or polarization maintaining optical fibers or a combination of various types. Furthermore, in addition to the Michelson configuration, the optical interferometer can also be in the form of a Mach-Zehnder or a combination of a Michelson and a Mach-Zehnder configuration, or any other optical interferometer configuration. The spinning disk can be placed in either the reference arm or the sample arm or any arm(s) of the interferometer to shift the optical phase. The optical spectrometer can be in various configurations, including, for example, the transmission grating configuration, the Littrow configuration and the curved reflective grating configuration.

It is well known to those skilled in the art that the optical phase delay of a light beam with a free-space wavelength $\lambda$, passing through an optical medium of refractive index n and thickness d, is equal to $$\Delta\phi = (2\pi/\lambda)nd, \quad (10)$$

Hence, changing either the refractive index or the thickness of the optical medium in the beam path can change the optical phase delay. In the case where the light beam is arranged to pass the same optical medium twice as illustrated in FIG. 1, the optical phase delay will be twice the value given by Eq. (10).

Figure 2A:
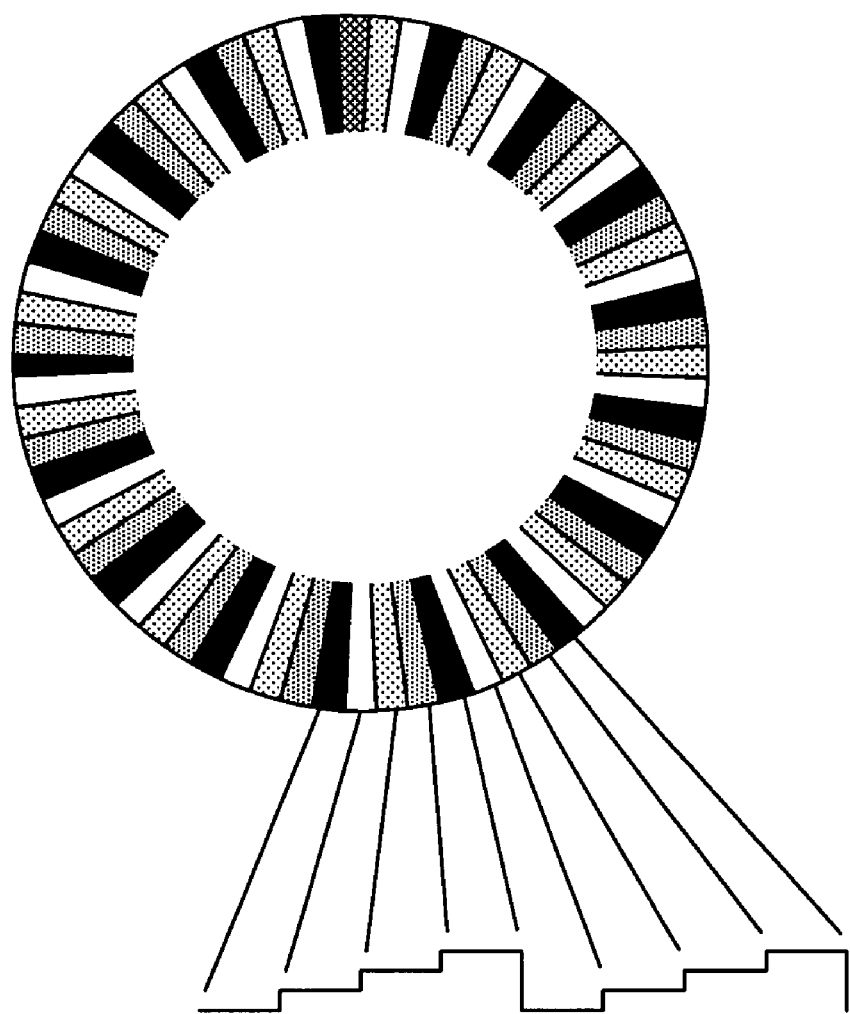
FIGS. 2A and 2B illustrate two examples of the invented phase shift disk.
Figure 2B:
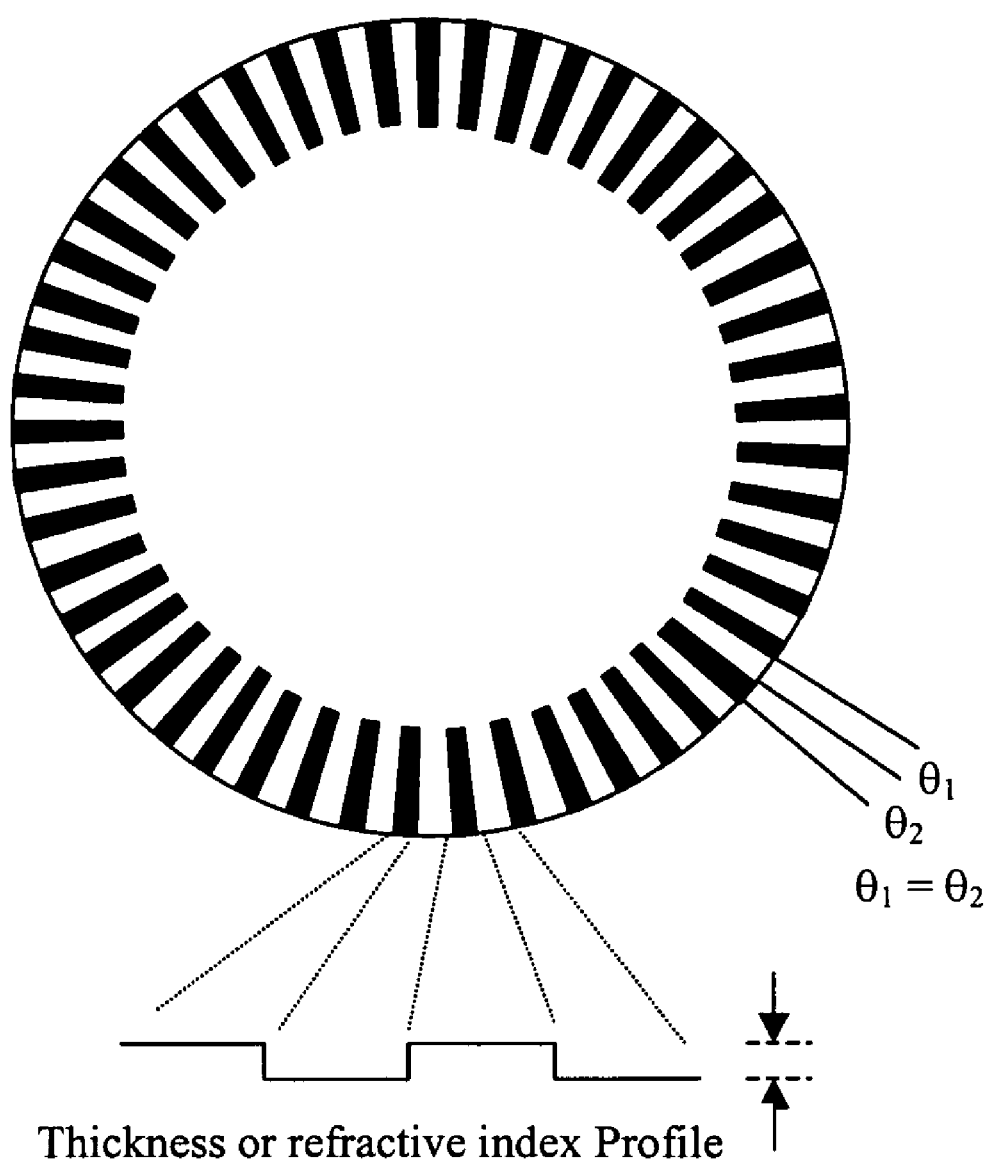
Figure 17:
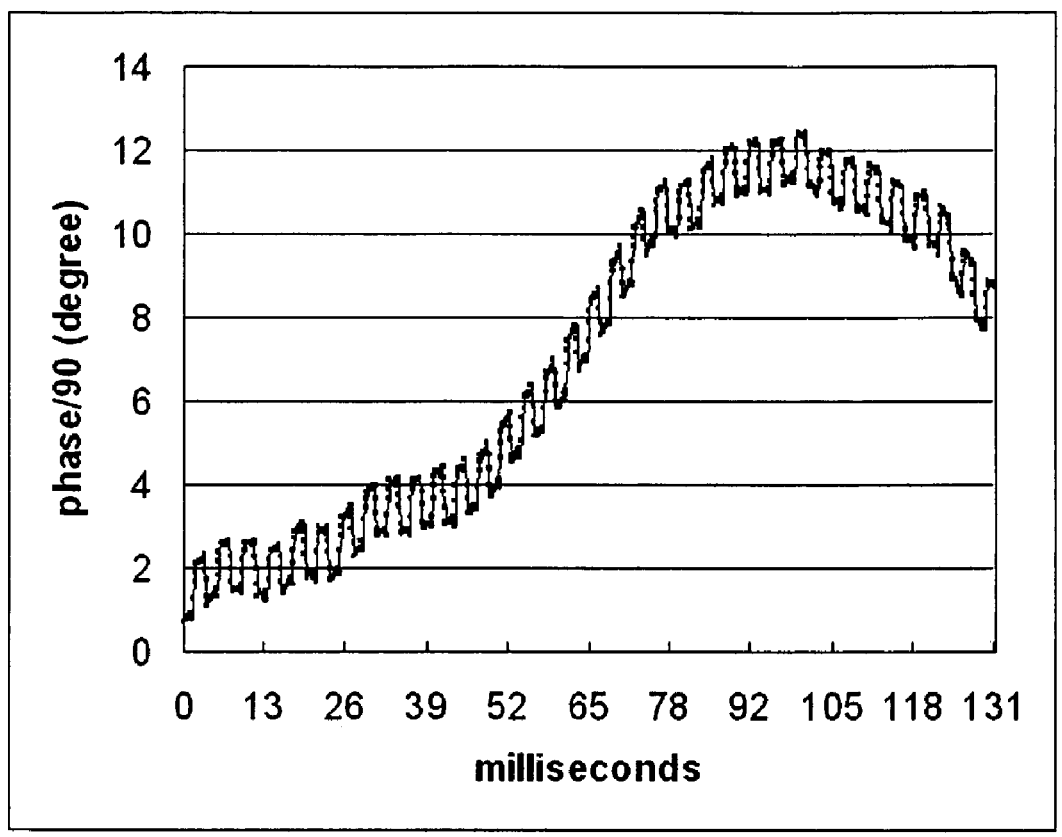
FIG. 17 shows the relative phase between the two arms of a SD-OCT system as a function of time for the case of a rotating 2-step phase shift disk.

FIGS. 2A and 2B illustrate two examples of the invented phase shift disk. In the illustrated embodiments, the disk contains radially striped patterns and the gray scale or darkness level of the stripes represents differences in optical phase delays. In FIG. 2A, 17 sets of 4 discrete phase shift stripes of substantially equal phase difference are shown and in FIG. 2B, a large number of 2 discrete phase shift stripes are illustrated. The optical phase delay variations among the different stripes are realized by either controlling the step height of the stripes or the refractive index distribution of the stripes as illustrated.

It should be understood that the number of sets and number of stripes per set can be varied. Although in a preferred embodiment, a relative phase difference of 90° or $\pi/2$ radian between two adjacent stripes is desired, the relative phase delay difference between adjacent stripes does not need to be equal and can have any value. In addition, the order of the phase shifts may also be varied. For example, the repeating sequence 0°, 180°, 270°, 90° has the advantage that as the disk spins, there are also larger phase shifts (180° rather than 90°) in comparison with potential movement of the subject. As will be elaborated in the disk fabrication section, this sequence also has advantages in terms of disk fabrication.

Briefly speaking, if extra thickness is deposited in two layers with the first layer providing 180° of phase shift over the second and third segments and the second layer providing 90° of phase shift over the third and fourth segments, then minor mask misalignments will not introduce new areas of unwanted phase shifts in such a pattern. FIGS. 3A and 3B shows two such examples of a 4 discrete phase shift arrangements.

As mentioned in the prior art section, phase shifted interferogram images can be used either for background subtraction (first image minus second image with a 180 degree phase shift between reference arm and sample arm) or for determining the full complex information for the spectral interferometry image (U.S. Pat. No. 6,377,349). A minimum of two images with a phase shift of 90 degrees can be utilized to get the full spectral information. Taking a series of images with a smaller sequential phase shift (for example, 6 images at 0, 30, 60, 90, 120, 150 degrees) improves the signal to noise ratio and accuracy of the measurement. If the disk is created such that the original phase image is repeated (for example, with images at 0°, 90°, 180°, 270°, 360°=0°), the first and last images should be identical if there is no movement of the sample. Assuming minimum acceleration, i.e. fixed velocity of the sample, the phase shift between the first and last image can be used to figure out the movement of the sample and hence to correct the effective phase of the remaining images.

A key advantage of obtaining multiple images with different phase shifts between the reference and sample arm is that it breaks the symmetry in the cross-correlation function, allowing one to distinguish between scattering in the sample arm from distances longer than the reference arm versus from distances shorter than the reference arm. Ideally the phase shift allows for measuring sample arm distances both longer and shorter than the reference arm. Alternatively, a simplified version of this approach can be used to readily identify features on the longer or the shorter reference arm side. The phase shift does not need to be restricted to specific values; instead, the features on the disk can have any relative optical path length difference, but typically some fraction of the scan range. When the image is acquired through these features, the images are translated axially. By observing whether the Fourier transformed spectrum distribution appears to shift closer to the DC line (for instance, zero distance where the sample and reference are path matched) or farther from the DC line, one can determine whether the sample or reference path length is longer. This can be determined either visually or automatically, and can provide a directional cue for adjusting the length of the reference or sample path to scan the sample within the valid scan depth of the instrument. In a preferred embodiment, the shift would occur with a modest duty cycle, such as at the beginning of a scan. By observing if the features moved closer to or farther from the DC line, the operator can determine whether to move instrument optics closer to the patient or farther away. Various combinations of changing the reference and sample arm lengths could be used to create this movement.

In terms of the shape of the phase shift patterns, they need not be restricted to consecutive radial stripes. They can be in any geometric shape, as long as the optical phase delay is maintained substantially constant when the light beam is entirely falling within a particular pattern.

In the case of a reflective arrangement where the light beam will pass through a height stepped phase shift disk twice as shown in FIG. 1, the relative optical phase delay difference between two adjacent steps is given by $$\Delta\phi = (2\pi/\lambda)2(n-1)h, \quad (11)$$

where n is the refractive index of the phase shift material at the wavelength of λ and h is the step height. Given a desired relative phase shift Δϕ, Eq. 11 can be used to determine the step height h of the corresponding phase shift pattern. Thus if the desired relative phase shift is 90° or π/2 radian, the required step height is given by $$h = \frac{\lambda}{8(n-1)} \quad (12)$$

It is preferred that the phase shift disk material is made from quartz or other optical material that is transparent over the range of the wavelength of the light source. In the illustration of FIG. 1, a separate mirror or reference reflector is placed behind the transparent disk. However, it should be understood that the disk can also be made reflective on either the front or the back surface of the spinning disk by, for example, depositing a highly reflective metal film there, and in the case of a reflective front surface, the disk material does not need to be transparent. However, the arrangement of combining a transparent phase shifter with a separate mirror as shown in FIG. 1 is preferred because as the disk rotates, it may wobble if the axis of spinning is not precisely aligned with the optical beam axis and in this case, if the reflective surface is directly on the front or back surface of the spinning disk, the reflected beam will also wobble in its backward propagation direction, which may affect the backward light coupling efficiency into the reference arm fiber. On the other hand, if a separate reference mirror is placed behind the disk, the wobbling of the disk will only slightly displace the beam in the transverse direction and will basically not affect the backward light coupling efficiency.

Another alternative feature made possible by the presently disclosed phase shifter is that it can also be used in a transmissive arm of an optical interferometer and in such a case, the relative optical phase shift required need to be twice that of the reflective case for the same amount of phase shift. It is well known to those skilled in the art that a light beam can be made to pass through the same optical disk a multiple number of times using a combination of transmissive and reflective configuration and for such a case, the step height of the phase shift stripe need to be adjusted accordingly.

Figure 4:
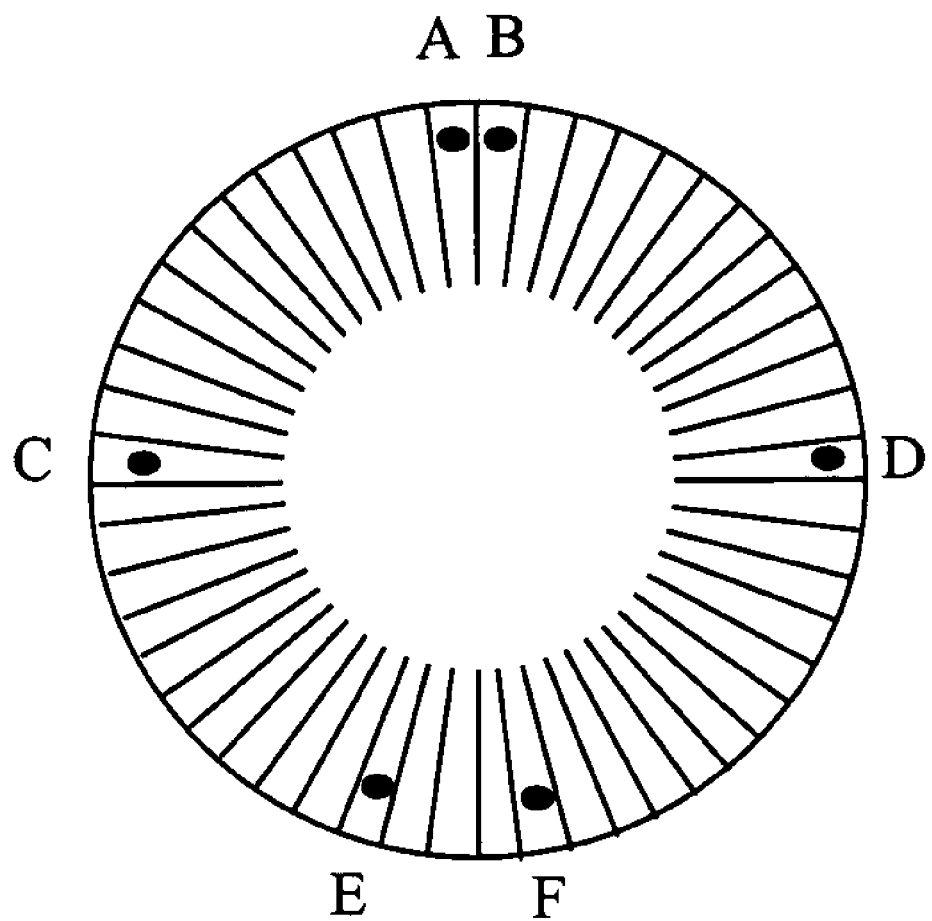
FIG. 4 shows some examples of beam passing positions through the same phase shift disk.
Figure 5:
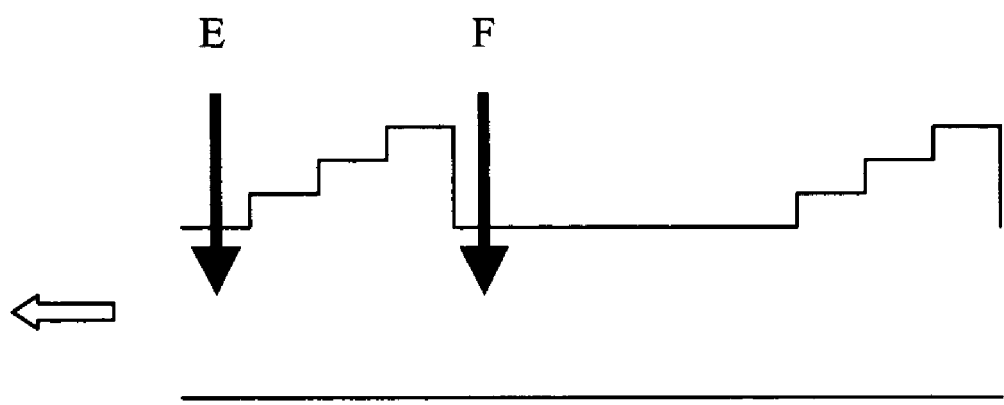
FIG. 5 shows an exemplary phase shift pattern design that will produce 4 discrete relative phase shifts between two beams passing through the same disk.

In addition to the possibility of placing the disk in only one of the two interferometer arms, it is also possible to let the two beams pass through the same disk at two different locations as shown in FIG. 4. For example, the two beams can be arranged to pass the disk through two neighboring phase shift pattern regions A and B. This is advantageous in that if the original disk substrate is not very parallel, the substrate thickness difference between two neighboring regions, and hence the relative phase difference in addition to the desired phase shift, will be much smaller than that between two farther away regions. In other words, since both beams pass through the same substrate, their instantaneous relative phase difference will be substantially determined by the relative step height and will not be markedly influenced the thickness variation over the whole substrate. On the other hand, if the substrate is initially substantially parallel, the two beams can be arranged to pass through the disk at two nearly opposing locations C and D. This will ease the alignment of the beams as the distance between C and D is now much larger than that between A and B. Alternatively, the two beams can also be arranged to pass through the disk at other possible locations. For example, if 4 discrete relative phase shifts are desired, an arrangement for the two beams to be separated by a 4 pattern distance as shown by E and F can be selected. In this case, the phase change steps between locations E and F can be made as shown in FIG. 5 so that as the disk spins, the relative phase difference between the two beam will have 4 discrete values.

Another feature of the present invention is that the phase shifting function can be combined with intensity modulation on the same disk, with both phase shifting and intensity modulation for the same beam or with phase shifting for one beam and intensity modulation for another or a combination of various phase and intensity modulation for multiple beams. Note that intensity modulation also includes the chopping of a light beam to generate light pulses or timing signals for synchronization. In addition, intensity modulation also includes a direct modulation of the light source.

By pulsing the beam through chopping or direct light source modulation, the measurement time can be limited to within a single acquisition period (reduced duty cycle) so as to minimize the blurring of the spectral domain interference fringes associated with movement of the sample such as an eye or the scan beam during acquisition. This is achieved by flashing the eye with a brief burst of light (just like strobe photography) rather than integrating continuous light signal over the acquisition time. In addition, as long as the repetition rate of the light pulse is above a threshold, while the average power of the light pulses shining onto a biological sample such as an eye should be maintained below a safety level, the peak power of the light pulse can be increased along with the reduction in the duty cycle of the pulse. It should be noted that light pulsing also helps in terms of transverse scanning (also called B-scan) speed in addition to timing. Up to now, SD-OCT systems have been limited in their transverse scan speed to a movement of less than the diffraction limited spot (movement of 5 microns) per image acquisition time (up to 30 k acquisitions/sec) to avoid blurring of the interference fringes. This over-sampling limits transverse scanning to approximately 150 mm/sec. Assuming a 5 mm transverse scan, this leads to a limitation of no more than 30 transverse or B-scans/sec, which is too low for effective 3-D image acquisition in a clinical setting. If one reduces the duty cycle by a factor of 5 with light beam chopping or direct light source intensity modulation, the transverse scanning speed can be increased by a factor of approximately 5, leading to 150 B-scans/sec, fast enough to generate a good 3-D data set. As the amount of time that the light beam is incident upon the eye is reduced, one should be able to increase the power, resulting in the same effective sensitivity. To maintain the same sensitivity, it is important to block or turn off the light in both the reference arm and sample arm simultaneously. One of the best ways to accomplish this is to place a chopper in the source arm or directly modulate the source. This can also be achieved by placing the chopper in the detector arm. However, this would not reduce the duty cycle of light incident upon the eye, which is important for safety considerations. One could put both the sample and reference arms through the chopper to simultaneously block them. This design might be preferable for a fiber optic system where the source arm has no portion in free space, but is more difficult to align.

Figure 6:
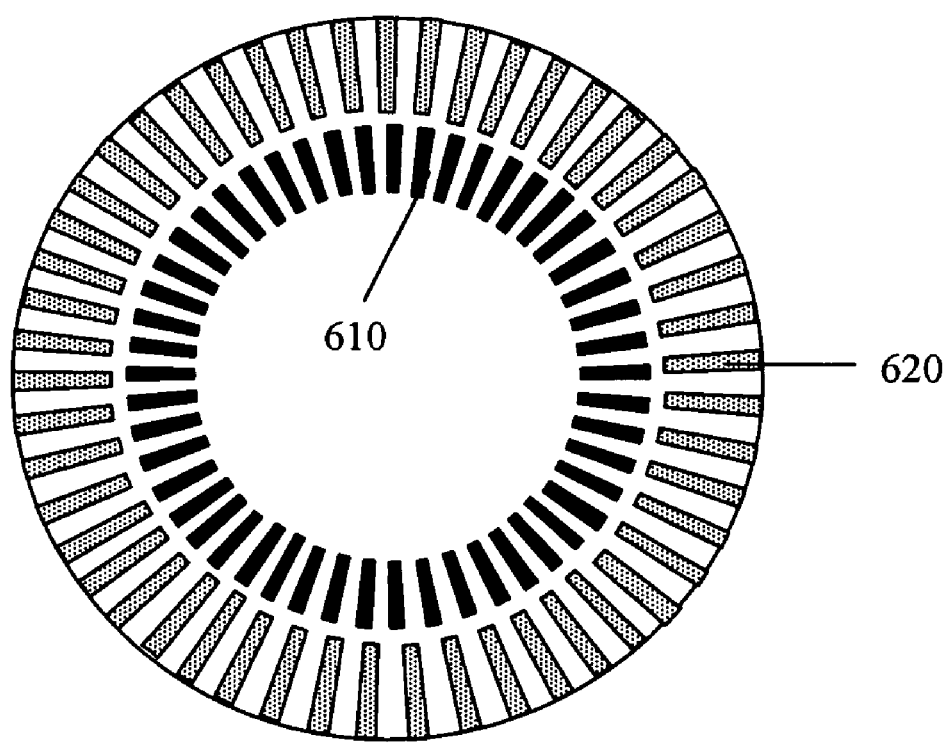
FIG. 6 shows an exemplary arrangement to make the phase shift and chopper patterns on the same disk where the chopper pattern is put at a different radius from the phase shift pattern.

In terms of the combination of both phase shifting and intensity modulation, one embodiment is to make the phase shift and chopper patterns on the same spinning disk to both reduce the acquisition time and obtain the benefits of the phase shifter in a single device. The easiest way to do this would be to put the chopper pattern 610 at a different radius from the phase shift pattern 620 and put the source arm through the chopper portion and the sample arm or reference arm through the phase shift portion as shown in FIG. 6. The chopper pattern can correspond to the step edge regions of the phase shift pattern to pulse the beam and synchronize it with the constant phase region.

Figure 7:
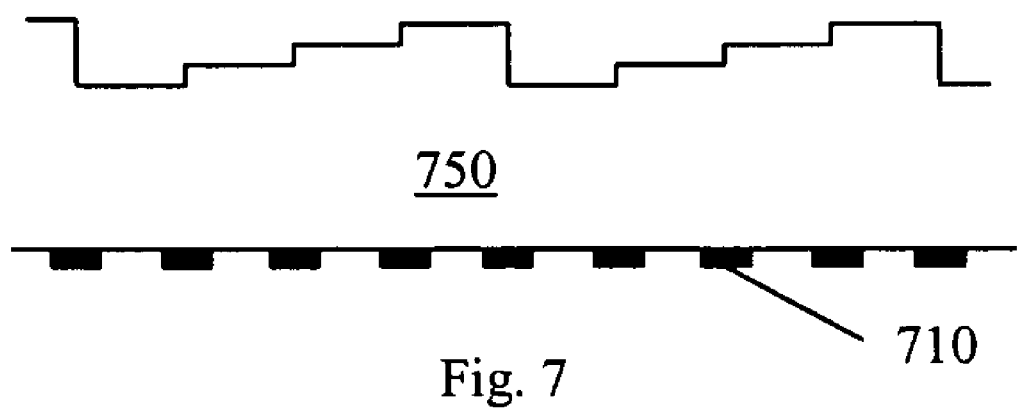
FIG. 7 shows another exemplary arrangement to make the phase shift and chopper patterns on the same spinning disk where the intensity modulation pattern is incidentally made on the other side of the disk at locations corresponding to the phase shift step edges.

For a single beam, opaque or partially transparent stripe patterns can be made on either the same phase pattern side or the other side of the disk with each opaque stripe corresponding to each phase shift step edge region to both strobe the light beam and also generate a timing signal for a synchronized data capturing of the phase shifted interferometric measurement. FIG. 7 shows the case where the intensity modulation pattern 710 is formed on one side of the disk 750 and the phase pattern is formed on the other side.

Figure 8:
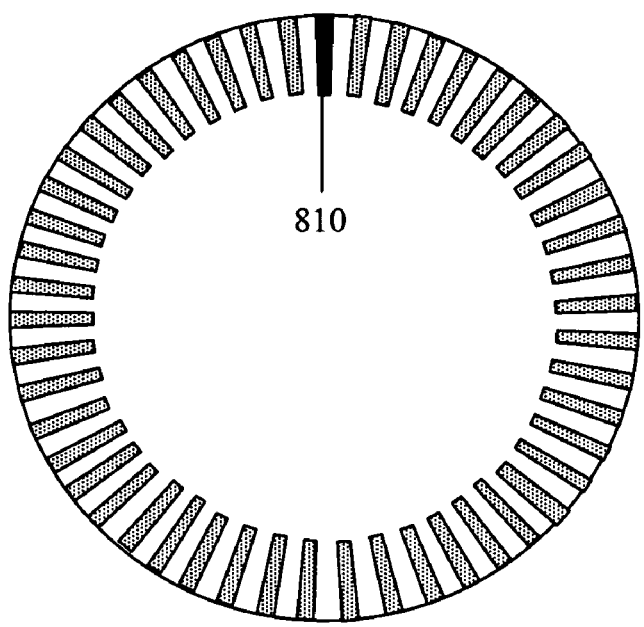
FIG. 8 shows still another exemplary arrangement to make the phase shift and chopper patterns on the same spinning disk where a single opaque stripe is made at the phase shift radius such that for each revolution, a timing signal is generated for synchronization.

Alternatively, as shown in FIG. 8, a single or a number of opaque stripe(s) 810 can be made for each revolution of the disk to generate timing signal(s) which can be used to directly modulate or pulse the broadband light source and to synchronize the data acquisition.

Figure 9A:
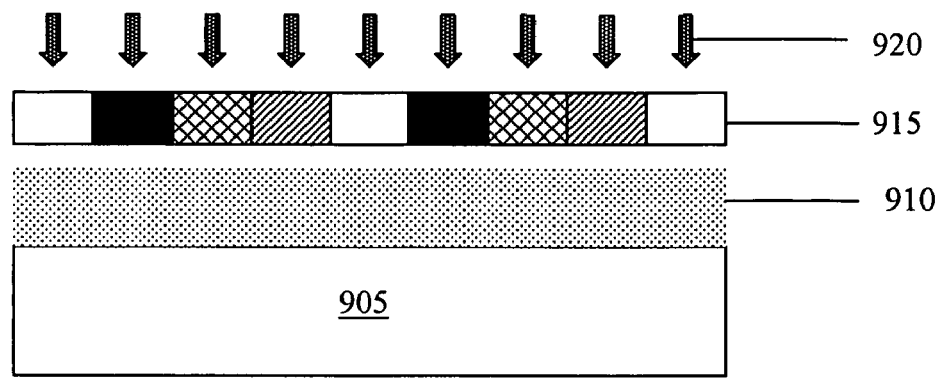
FIGS. 9A to 9C show one exemplary method to fabricate the phase shift disk in which a gray scale mask and dry etching are employed.
Figure 9B:
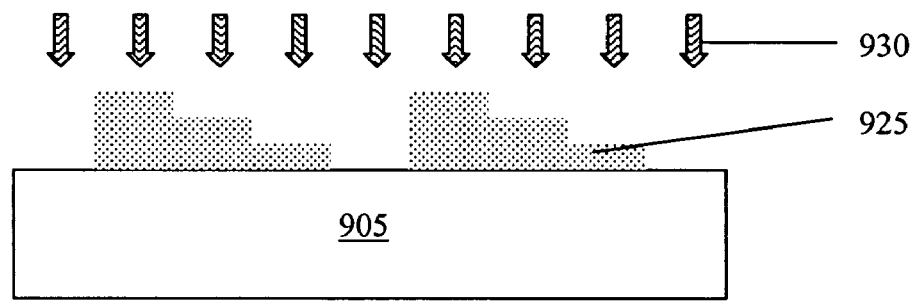
Figure 9C:
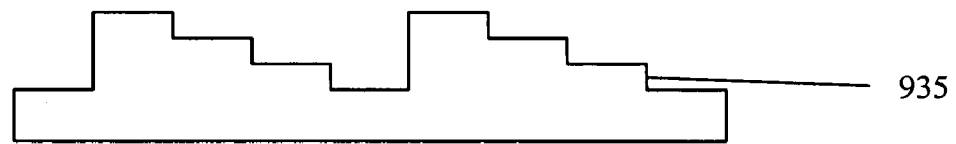

There are numerous possible ways to fabricate the subject phase shift disk. One approach is to directly etch the desired step patterns into the substrate using photolithography and wet or dry etching. FIG. 9 shows one embodiment that involves the use of a gray scale mask and dry etching. In brief, a photoresist layer 910 is firstly spin-coated on the substrate 905 and a gray scale mask 915 is used for UV exposure 920 (FIG. 9A). After development, the photoresist will have stepped thickness variations 925 (FIG. 9B). Dry etching 930 can be used to transfer the photoresist pattern 925 into the substrate material 905. The end result will be a stepped pattern 935 made in the substrate (FIG. 9C).

A potential shortcoming associated with gray scale mask based photolithography is that the UV exposure may not be uniform and typically there is a variation of up to a few percent in terms of the UV illumination uniformity across a wafer. As a result, after development, the stepped photoresist pattern 925 will have height errors across the wafer and this will be transferred to the substrate 905. If the disk is small and is placed near the center of the expanded UV exposure beam, the variation may be less. In addition, a gray scale mask is generally much more expensive than an ordinary mask.

As an alternative, instead of using a gray-scale mask, multiple exposure and etching such as used for binary optics element fabrication may be employed and this is illustrated in FIG. 10. With a first photoresist layer 1010 spin-coated on the substrate 1005, a first mask 1015 can be used to expose the photoresist 1010 with UV light 1020 (FIG. 10A), which will produce a photoresist pattern 1030 (FIG. 10B). Assuming that equal step height patterns are to be made, either dry or wet etching 1025 can be used to firstly etch the substrate 1005 for twice as deep as the desired step height to form the ridge pattern 1035 (FIG. 10C). Following photoresist removal, a new photoresist layer 1040 can be spin-coated on the surface of the ridged pattern 1035 and a second mask 1045 is aligned (with the help of some alignment marks) with respect to the etched pattern 1035 for a second UV exposure 1050. After development, a photoresist pattern 1055 will be formed (FIG. 10D) and a second wet or dry etching 1060 removes the substrate material for a depth equal to the desired step height. Once the second photoresist is removed, the substrate will have the desired stepped phase shift pattern 1065 (FIG. 10E).

A potential issue associated with this approach is that during the second UV exposure 1050, the second mask 1045 may not be precisely aligned with the first etched pattern 1035 and if this is the case, there is a possibility that narrow trenches or hills will be formed in the step regions. However, if the phase shift pattern is in the sequence as shown in FIG. 3, a slight misalignment will not create the narrow trenches or hills. This is shown in FIG. 11, which is the same as FIG. 10 (and like elements have the same numbers) except that the new second mask 1145 now has a stripe pattern as wide as the first mask 1015 and during alignment, the first etched steps 1170 and 1175 are completely covered or not covered by the second mask stripe patterns. The final pattern 1165 has the same number of steps as pattern 1065 of FIG. 10 but in a different order.

It should be pointed out that even with the approach shown in FIG. 11, another potential issue is that the etching (either wet or dry) may not be uniform and in addition, as there are no etch-stop layers, precise control of the etch-depth can be a problem. It is well known to those skilled in the art that while wet and dry etching without an etch-stop layer is not very uniform and it is difficult to control the etch depth to within nanometer precision, dry etching is also generally very expensive.

As a solution to these problems, FIG. 12 shows a preferred disk fabrication embodiment of the present invention. Instead of directly etching into the substrate material, layers for both etch-stop and phase change purposes are deposited and patterned on the substrate. Owing to the fact that deposition of multiple layers of sub-micron optical films with a thickness precision down to the one-nanometer level over a large area has been well-established for the optical fiber telecom industry, this technology can thus be used for the subject phase shift disk fabrication. As shown in FIG. 12A, an etch-stop thin layer 1204 of, for example, 30 nm to 40 nm of silicon nitride, can be firstly deposited on both sides of a substrate 1202. A 180° phase shift layer 1206 of, for example, silicon dioxide, can be deposited on top of the etch-stop layer 1204. After a photoresist layer 1208 is spin-coated on the 180° phase shift layer 1206, a first mask 1210 can be used for the first UV exposure 1211. With development, photoresist pattern 1212 (FIG. 12B) is created and the unprotected regions of the 180° phase shift layer can be wet or dry etched (1213). Due to the fact that there is an underlying etch-stop layer 1204, the phase shift value will be precisely determined by the deposited film thickness of layer 1206. While a dry etching process may produce a better sidewall for the etched step, given that the width of the phase shift stripes (of the order of about 1 mm) is generally much lager than their height (of the order of sub-micron) and the cost of dry etching is much higher than that of wet etching, consequently, wet etching is preferred. Note that due to the existence of the etch-stop layer 1204 on the bottom side of the substrate, both sides of the substrate are protected during the wet etching process. After the removal of the photoresist pattern 1212, a second etch-stop layer 1214 and a 90° phase shift layer 1216 can be deposited on the topside of the disk (FIG. 12C). A second layer of photoresist 1218 can be spin-coated and a second mask 1220 can be aligned with the etched patterns to UV expose (1221) the second photoresist layer 1218 (FIG. 12D). After development, a second photoresist pattern 1222 will be created (FIG. 12E), which can be used for etching (1225) the 90° phase shift pattern 1224 (FIG. 12F). Note that in spite of the existence of the etch-stop layers 1204 and 1214, the relative phase shift is solely determined by the thickness of the deposited phase shift layer(s) since all phase shift patterns will be coated with the same number and hence the same thickness of the etch-stop layers. The fact that the etch-stop layers are very thin, each with a thickness of 30 nm to 40 nm, which is much smaller than the light wavelength, ensures that there will be negligible reflection of light from the interfaces created by these layers.

It should be noted that in addition to what has been illustrated in FIG. 12, the same concept of using deposition and photolithography to create the phase shift layers and patterns can be extended to other possible ways to fabricate the same.

Figure 13A:
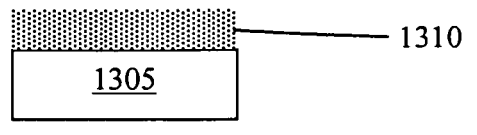
FIGS. 13A to 13J show another exemplary method to fabricate the phase shift disk in which lift-off instead of etching is employed.
Figure 13B:
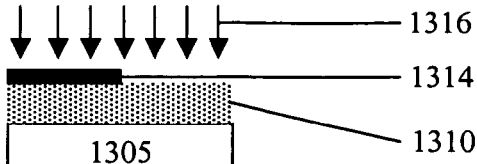
Figure 13C:
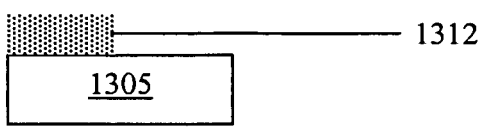
Figure 13D:
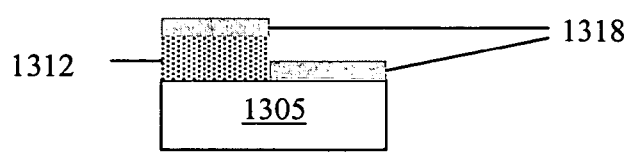
Figure 13E:
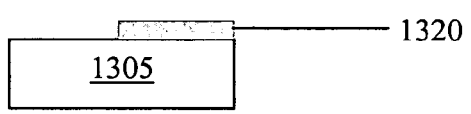
Figure 13F:
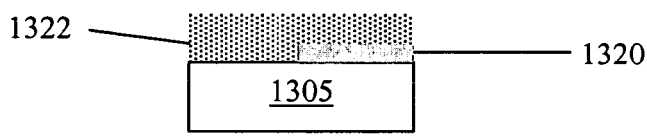
Figure 13G:
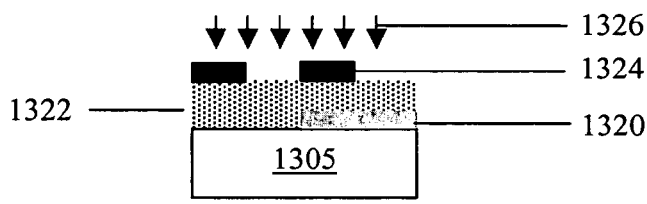
Figure 13H:
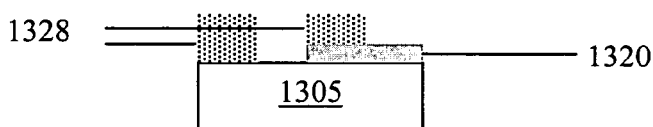
Figure 13I:
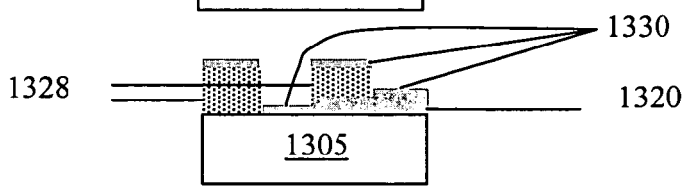
Figure 13J:
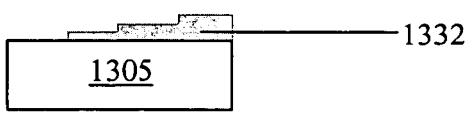

For example, instead of etching the deposited phase shift layer, a lift-off process can be utilized. As shown in FIG. 13A, a photoresist layer 1310 can be spin-coated on the substrate 1305 and a photoresist pattern 1312 can be created using a first mask 1314 and UV exposure 1316 (FIGS. 13B and 13C), which can be followed by the deposition of a first 180° phase shift layer 1318 (FIG. 13D). Typically as long as the photoresist layer 1310 (and hence the photoresist pattern 1312) is more than twice as thick as the deposited 180° phase shift layer 1318 (which is generally the case for the intended phase shift of the invention), a ridged phase shift pattern 1320 can be created by lifting-off the photoresist pattern 1312 (FIG. 13E). The lift-off process requires that the sidewall of the photoresist pattern 1312 be relative vertical or T-shaped and this can be achieved using for example image reversal. A second photoresist layer 1322 can then be spin-coated (FIG. 13F) and a second mask 1324 used together with a second UV exposure 1326 and photoresist development to create the second photoresist pattern 1328 (FIGS. 13G and 13H). After the deposition of a 90° phase shift layer 1330 (FIG. 13I), the photoresist pattern 1328 can be lifted-off to create the desired phase shift pattern 1332 (FIG. 13J).

The advantage of the lift-off process is that there is no need to deposit the etch-stop layers as illustrated in FIG. 12. However, this process requires the proper sidewall control and, most preferably, T-shaping of the photoresist and also preferably a directional deposition of the phase shift material. Another disadvantage is the requirement of a low temperature phase shift layer deposition process due to the fact that the photoresist generally cannot withstand a temperature higher than 120° C. With a low temperature deposition, the deposited film may not be dense enough or may not adhere well enough to the substrate. Although, a metal pattern instead of a photoresist pattern can be used for lift-off, this will complicate process and hence increase the cost of fabrication.

It should be noted that in the above-mentioned disk fabrication methods, when wet etching is employed, an etch-stop layer can always be deposited on the other side of the substrate to prevent the substrate material from being etched way from the other side.

It should also be noted that in the above-mentioned disk fabrication methods, the wet or dry etch protective pattern does not need to be restricted to photoresist patterns, in fact some other materials such as metals or dielectrics are more frequently used as dry etch caps and such a pattern can be created using photolithography and etch or lift-off.

Figure 14A:
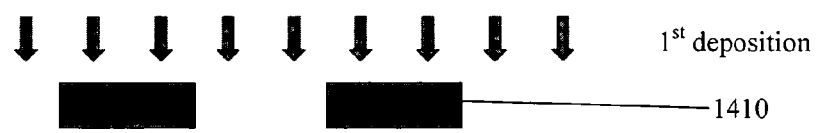
FIGS. 14A to 14D show still another exemplary method to fabricate the phase shift disk in which metal shadow masks are used to directly create phase shift patterns.
Figure 14B:
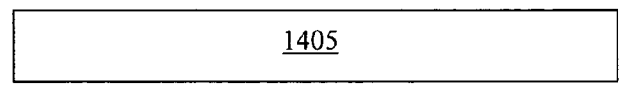
Figure 14C:
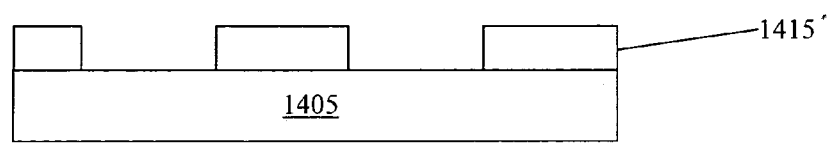
Figure 14D:
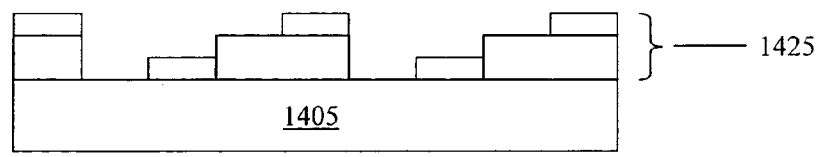

Another possible approach is to use a metal shadow mask in the deposition chamber to directly create phase shift ridges. As shown in FIG. 14, a first shadow mask 1410 can be used for the deposition of the 180° phase shift ridges 1415 on the substrate 1405 (FIGS. 14A and 14B) and this process can be repeated with a second shadow mask 1420 that needs to be properly aligned to create the desired multiple step patterns 1425 (FIGS. 14C and 14D). The advantage of this process is that it is simple and since a metal shadow mask can withstand high temperature, the deposited film can be dense and can adhere well to the substrate. However, the requirement on the alignment of the second shadow mask may make the process tedious and complicated. In addition, due to the gradual accumulation of the deposited material on the shadow masks, they can only be used for a limited number of times.

Figure 15A:
FIGS. 15A to 15C show still another exemplary method to fabricate the phase shift disk in which the embossing/stamping/molding technique is used together with thermal or UV curing to directly create phase shift patterns.
Figure 15B:
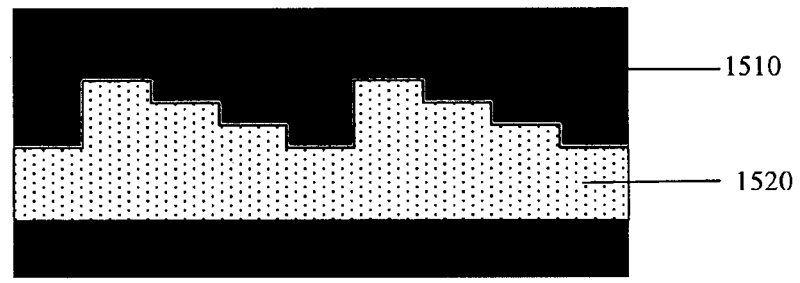
Figure 15C:
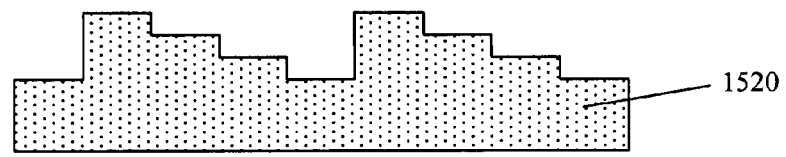

To further reduce the cost of fabrication, especially when large volume production is needed, another alternative is to use the embossing/stamping/molding technique as used for CDs or DVDs or holographic films to fabricate the phase shift disk. As shown in FIG. 15, a master stamp 1510 (FIG. 15A) that has the negative three dimensional structure of the desired phase shift patterns can firstly be made using advanced high precision machining such as diamond turning. Thermal or UV curable polymers, including purely organic materials such as polystyrene or polycarbonate, purely inorganic materials such as sol-gel glass, or a combination of organic and inorganic materials such as ormosils, can be molded either directly into the form of a phase shift disk 1520 (FIGS. 15B and 15C) or onto a substrate to form the phase shift disk.

It should be understood that the illustrated embodiments in terms of the fabrication of the invented phase shift disk are only exemplary. In fact, we have made such phase shift disks using the fabrication principles illustrated in FIG. 12.

Figure 16:
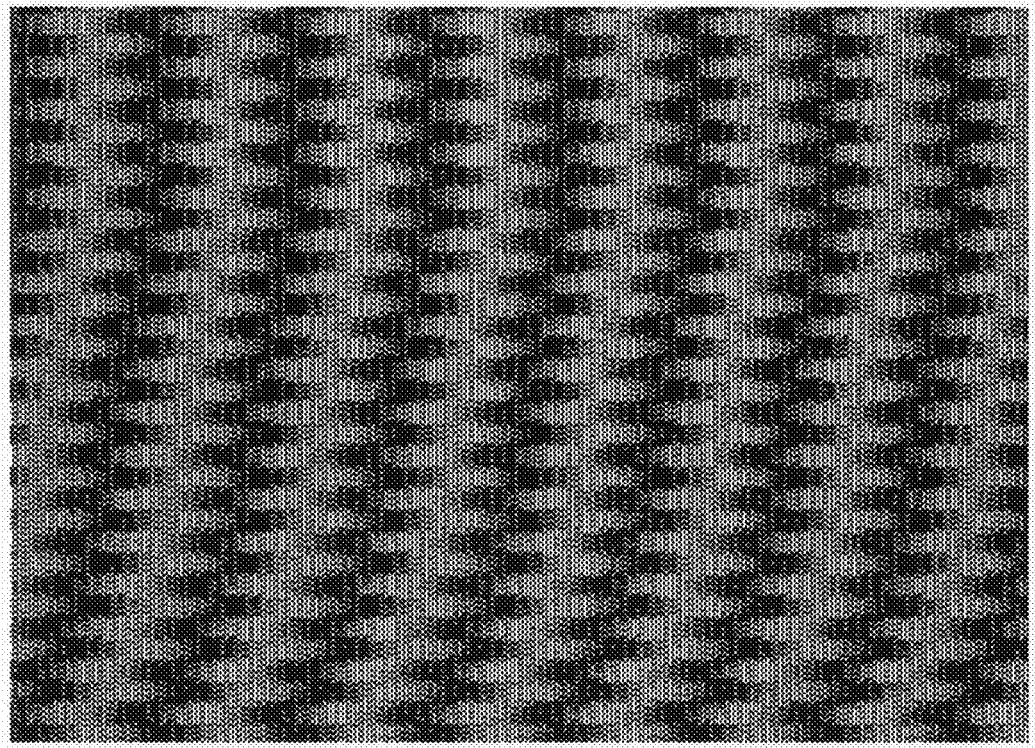
FIGS. 16A and B show the spectral domain interferogram images of a 2-step and 4-step phase shift disks respectively, captured by a line scan camera.
Figure 16:
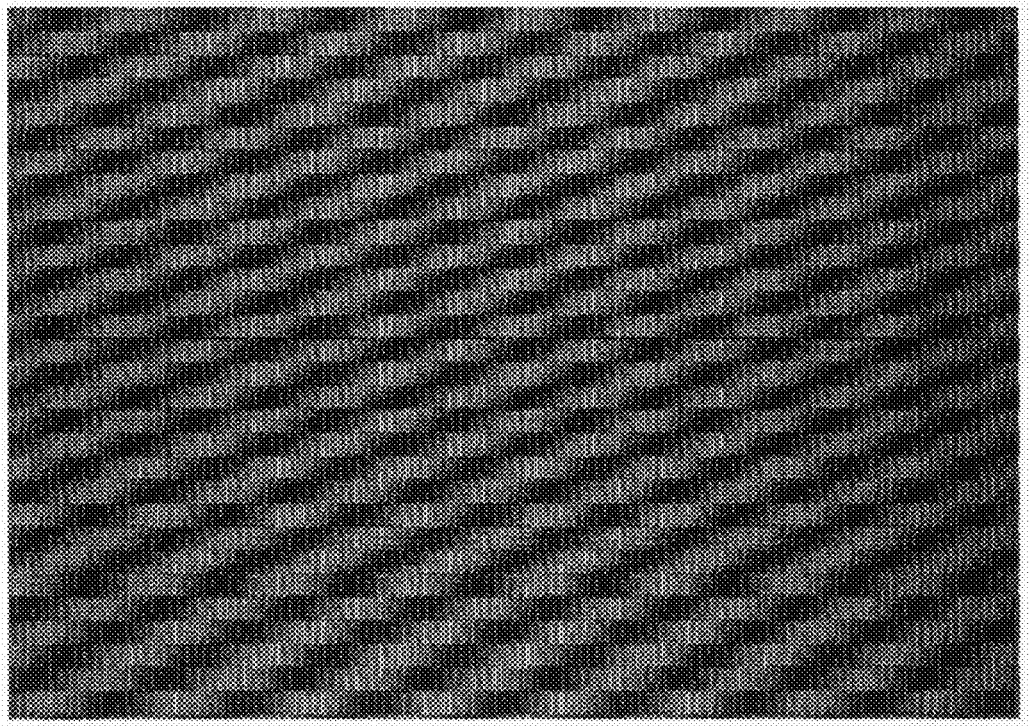

In order to test the performance of the fabricated phase shift disks, a configuration as illustrated in FIG. 1 was set up in which the sample is just a mirror, and a line scan camera was used to capture the spectral domain interferogram images when the phase shift disk is rotated relatively slowly. FIGS. 16A and 16B show the line scan camera images of the 2-step and 4-step phase shift disks respectively. Note that the horizontal axis shows the intensity distribution of the spectral domain interferograms along the detector array and the vertical axis represents time or the beam position on the phase shift disk as it rotates. From these images, it can be seen that there are abrupt lateral positional shift of the interferogram and hence abrupt relative phase jumps between the two interferometer arms as a function of time. By comparing the relative lateral positional shift of a particular bright fringe across a phase shift step with the lateral distance between two neighboring bright fringes, it can also be seen that the laterally shifted distance is about a quarter of the period of the interference fringe pattern, which means that the relative phase shift is about 90° for both the 2-step and the 4-step phase shift disk. By tracing the interference fringe patterns vertically, it can be seen that the fringes of supposedly constant relative phase do not produce vertically overlapping interferograms, which means that relative phase between the two interferometer arms is slowly changing in addition to the abrupt jump. This can be caused by various factors that can slowly change the relative optical path length between the two interferometer arms, such as people moving in the lab or the mechanical vibration of other instruments, and room temperature variation.

FIG. 17 shows the relative phase between the two arms of a SD-OCT system as a function of time for the case of a rotating 2-step phase shift disk. The relative phase is obtained by Fourier-transforming the spectral interferogram together with other digital data processing. The vertical axis is the relative phase in a unit of every 90° and the horizontal axis is time. Again, it can be seen that in addition to the expected abrupt phase shift, there is also a slowly varying relative phase or optical path length that can be caused by the above-mentioned various factors.

In order to test the performance of the fabricated phase shift disks, a configuration as illustrated in FIG. 1 was set up in which the sample is just a mirror, and a line scan camera was used to capture the spectral domain interferogram images when the phase shift disk is rotated relatively slowly. FIGS. 17A and 17B show the line scan camera images of the 2-step and 4-step phase shift disks respectively. Note that the horizontal axis shows the intensity distribution of the spectral domain interferograms along the detector array and the vertical axis represents time or the beam position on the phase shift disk as it rotates. From these images, it can be seen that there are abrupt lateral positional shift of the interferogram and hence abrupt relative phase jumps between the two interferometer arms as a function of time. By comparing the relative lateral positional shift of a particular bright fringe across a phase shift step with the lateral distance between two neighboring bright fringes, it can also be seen that the laterally shifted distance is about a quarter of the period of the interference fringe pattern, which means that the relative phase shift is about 90° for both the 2-step and the 4-step phase shift disk. By tracing the interference fringe patterns vertically, it can be seen that the fringes of supposedly constant relative phase do not produce vertically overlapping interferograms, which means that relative phase between the two interferometer arms is slowly changing in addition to the abrupt jump. This can be caused by various factors that can slowly change the relative optical path length between the two interferometer arms, such as people moving in the lab or the mechanical vibration of other instruments, and room temperature variation.

FIG. 18 shows the relative phase between the two arms of a SD-OCT system as a function of time for the case of a rotating 2-step phase shift disk. The relative phase is obtained by Fourier-transforming the spectral interferogram together with other digital data processing. The vertical axis is the relative phase in a unit of every 90° and the horizontal axis is time. Again, it can be seen that in addition to the expected abrupt phase shift, there is also a slowly varying relative phase or optical path length that can be caused by the above-mentioned various factors.

Note that although the invented phase shift disk is described for its application in spectral domain OCT systems, it can also be used for other optical systems as long as there is a need to abruptly change the phase of an optical beam in free space, especially in discrete phase steps. Therefore, its application should not be restricted to spectral domain OCT systems.

In addition to varying the thickness of the disk material, it should be noted that the optical phase shift patterns can also be created by varying the refractive index of the material in two or more regions. Exemplary methods include radiation (such as UV light) induced refractive index change in photosensitive glass, ion-implantation induced refractive index change, and doping induced refractive index change such as that from the ion-exchange process. At the present time, it may be difficult to economically achieve the desired uniformity of the phase shift patterns with the latter approaches. However, the subject invention is intended to include a phase shift disk which includes variations in index of refraction.

Of course, it would be possible to create a disk with regions having different thicknesses and indices of refraction. For example, a substrate can be formed with two regions having different indices of refraction and a lithographic/deposition technique can be used to add two or more regions of different thicknesses on top of the substrate. Alternatively, a lithographic/deposition technique could be used to deposit different materials in different regions with different thickness and different indices of refraction.

The foregoing description of the invention is presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the particular use contemplated.

The following references are incorporated herein by reference:

U.S. PATENT DOCUMENTS

U.S. Pat. No. 5,321,501, Swanson, et al. "Method and apparatus for optical imaging with means for controlling the longitudinal range of the sample"

U.S. Pat. No. 5,459,570, Swanson, et al. "Method and apparatus for performing optical measurements"

U.S. Pat. No. 5,491,524, Hellmuth, T. and J. Wei "Optical coherence tomography corneal mapping apparatus";

U.S. Pat. No. 6,111,645, Tearney, et al. "Grating based phase control optical delay line"

U.S. Pat. No. 6,282,011, Tearney, et al. "Grating based phase control optical delay line"

U.S. Pat. No. 6,377,349, Fercher, "Arrangement for spectral interferometric optical tomography and surface profile measurement"

OTHER PUBLICATIONS

Chen, N. G. and Q. Zhu (2002). "Rotary mirror array for high-speed optical coherence tomography." Optics Letters 27(8): 607-609;

De-Boer, J. F., et al. (2003). "Improved signal-to-noise ratio in spectral-domain compared with time-domain optical coherence tomography." Optics Letters 28(21): 2067-2069;

Fercher, A. F. et al. (1995). "Measurement of intraocular distances by backscattering spectral interferometry." Optics Communications 117(1-2): 43-48;

Fujimoto, J. G. "Optical coherence tomography for ultrahigh resolution in vivo imaging." Nat Biotechnol 21(11): 1361-7, (2003);

Huang, D. et al. (1991). "Optical coherence tomography." Science 254 (5035): 1178-81;

Lai, M. (2001). "Kilohertz Scanning Optical Delay Line Employing a Prism Array." Applied Optics 40(34): 6334-6336;

Leitgeb, R. A., et al. (2003). "Phase-shifting algorithm to achieve high-speed long-depth-range probing by frequency-domain optical coherence tomography." Optics Letters 28(22): 2201-2203;

Leitgeb, R. A., et al. (2003). "Performance of Fourier domain vs. time domain optical coherence tomography." Optics Express 11(8): 889-894;

Smith, L. M. and C. C. Dobson (1989). "Absolute displacement measurements using modulation of the spectrum of white light in a Michelson interferometer." Applied Optics 28(15): 3339-3342

Vakhtin, A. B., et al. (2003). "Differential spectral interferometry: an imaging technique for biomedical applications." Optics Letters 28(15): 1332-1334;

Wojtkowski, M., et al. (2003). "Real-time in vivo imaging by high-speed spectral optical coherence tomography." Optics Letters 28(19): 1745-1747;

Wojtkowski, M., et al. (2002) "Full range complex spectral optical coherence tomography technique in eye imaging." Optics Letters 27(16): 1415-1417.

We claim:

1. A spectral domain optical coherence tomography (SD-OCT) system comprising:

a broadband radiation source;

an optical interferometer having a source path for receiving light from the radiation source, a sample path which directs a portion of the radiation to the sample, a reference path and a detection path;

a spectrometer for receiving and measuring combined light from the sample and detection paths and generating output signals in response thereto;

a rotatable disk located in at least one of the paths of the interferometer, said disk having a radially oriented pattern of regions formed thereon such that when the disk rotates, a beam of light incident upon the disk will undergo different optical phase delays as it impinges upon different regions of the disk; and a processor for deriving a complex spectral interferogram based on the generated output signals.

2. A system as recited in claim 1, wherein a first set of regions of said disk is configured to create a first phase delay in the light interacting therewith and a second set of regions of said disk is configured to create a second, different phase delay in the light interacting therewith.

3. A system as recited in claim 2, wherein said disk includes a set of third regions configured to create a phase delay of light different from said first and second regions.

4. A system as recited in claim 2, wherein the difference in the phase delay created by the first and second regions of the disk is 90 degrees.

5. A system as recited in claim 3, wherein said disk includes a set of fourth regions configured to create a phase delay of light different from said first, second and third regions.

6. A system as recited in claim 3, wherein said disk includes n sets of regions, each set configured to create a different phase delay of light.

7. A system as recited in claim 5, wherein the phase delays created by the second regions is 90 degrees greater than the first region, and the phase delay created by the third region is 90 degrees greater than the second region and the phase delay created by the fourth regions is 90 degrees greater than the third region.

8. A system as recited in claim 7, where the regions are arranged about the disk in a repeating pattern with the fourth regions following the third regions which in turn follow the second regions which in turn follow the first regions.

9. A system as recited in claim 7, where the regions are arranged about the disk in a repeating pattern with the second regions following the fourth regions which in turn follow the third regions which in turn follow the first regions.

10. A system as recited in claim 1, wherein the difference in the phase delay in the regions of the disk is the result of different thicknesses in the direction parallel to the path of the light in the respective regions.

11. A system as recited in claim 1, wherein the difference in the phase delay in the regions of the disk is the result of different step height in the direction parallel to the path of the light in the respective regions.

12. A system as recited in claim 1, wherein the difference in the phase delay in the regions of the disk is the result of different indices of refraction in the respective regions.

13. A system as recited in claim 1, wherein the difference in the phase delay in the regions of the disk is the result of a combination of differences in the thicknesses, step height and indices of refraction in the respective regions.

14. A system as recited in claim 1, wherein the disk is formed on a quartz substrate.

15. A system as recited in claim 1, wherein said disk includes a reflective coating on the front surface thereof.

16. A system as recited in 1, wherein said disk is transmissive.

17. A system as recited in claim 16, wherein said disk includes a reflective coating on the rear surface opposed to the surface at which light enters the transmissive disk.

18. A system as recited in claim 1, wherein said disk also contains at least one region for attenuating light.

19. A system as recited in claim 1, wherein said disk further includes a radial pattern of light attenuating regions.

20. A system as recited in 19, wherein the radial pattern of light attenuating regions is located generally at the same radius as the pattern of phase delay regions.

21. A system as recited in the 19, wherein said radial pattern of light attenuating regions is located either radially inwardly or outwardly with respect the pattern of phase delay regions.

22. A system as recited in claim 1, wherein said disk is fabricated by one or more processes selected from the group consisting of gray scale mask based photolithography, standard photolithography, wet etching, dry etching, multiple etch-stop and phase shift film deposition, lift-off, shadow mask based patterned film deposition, embossing, stamping and molding.

23. A system as recited in claim 1, further including means to modulate the intensity of the radiation reaching the spectrometer.

24. A system as recited in claim 23, wherein the means of modulating the intensity of the radiation is performed by directly modulating the source.

25. A system as recited in claim 23, wherein said means for modulating the intensity of the radiation comprises forming a pattern of radiation attenuating regions on the disk.

26. A system as recited in claim 23, wherein said means for modulating the intensity of the radiation includes an intensity modulating chopper disk operated in synchronization with said rotatable disk.

27. A method of obtaining spectral domain optical coherence tomograms of a sample comprising the steps of:

guiding radiation from a broadband light source into an interferometer having a sample path directing a portion of the radiation to the sample and a reference path and a detection path;

combining returned radiation from the sample and reference paths and measuring the combined radiation with a spectrometer to generate output signals;

inducing repetitive relative phase shifts in the radiation by causing said radiation to interact with a rotating disk having a radially oriented pattern of regions formed thereon such that when the disk rotates, a beam of light incident upon the disk will undergo different optical phase delays as it impinges upon different regions of the disk; and processing the output signals to derive a complex spectral interferogram in order to generate spectral domain coherence tomograms of the sample.

28. A method as recited in claim 27, wherein said phase shifting is synchronized with the measurements.

29. A method as recited in claim 27, further including the step of modulating the intensity of the radiation.

30. A method as recited in claim 29, wherein the step of modulating the intensity of the radiation is performed by directly modulating the source.

31. A method as recited in claim 27, wherein the disk further includes a radial pattern of radiation attenuating regions for modulating the intensity of the radiation.

32. A method as recited in claim 31, wherein the radial pattern of light attenuating regions is located generally at the same radius as the pattern of phase delay regions.

33. A method as recited in claim 31, wherein said radial pattern of light attenuating regions is located either radially inwardly or outwardly with respect to said pattern of phase delay regions.

34. A method as recited in claim 27, wherein a first set of regions of said disk is configured to create a first phase delay in the light interacting therewith and a second set of regions of said disks is configured to create a second, different phase delay in the light interacting therewith.

35. A method as recited in claim 34, wherein said disk includes a set of third regions configured to create a phase delay of light different from said first and second regions.

36. A method as recited in claim 34, wherein the difference in the phase delay created by the first and second regions of the disk is 90 degrees.

37. A method as recited in claim 35, wherein said disk includes a set of fourth regions configured to create a phase delay of light different from said first, second and third regions.

38. A method as recited in claim 35, wherein said disk includes n sets of regions, each set configured to create a different phase delay of light.

39. A method as recited in claim 37, wherein the phase delays created by the second regions is 90 degrees greater than the first region, and the phase delay created by the third region is 90 degrees greater than the second region and the phase delay created by the fourth regions is 90 degrees greater than the third region.

40. A method as recited in claim 27, wherein the difference in the phase delay in the regions is the result of a combination of differences in the thicknesses, step height and indices of refraction in the respective regions.

41. A method as recited in 27, wherein said disk is transmissive.

* * * * *